(12) United States Patent
Schabbach

(10) Patent No.: US 10,973,980 B2
(45) Date of Patent: Apr. 13, 2021

(54) DOSE INDICATING MECHANISM FOR A DRUG DELIVERY DEVICE AND DRUG DELIVERY DEVICE

(71) Applicant: SANOFI-AVENTIS DEUTSCHLAND GMBH, Frankfurt am Main (DE)

(72) Inventor: Michael Schabbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 103 days.

(21) Appl. No.: 15/313,431

(22) PCT Filed: May 27, 2015

(86) PCT No.: PCT/EP2015/061619
§ 371 (c)(1),
(2) Date: Nov. 22, 2016

(87) PCT Pub. No.: WO2015/181187
PCT Pub. Date: Dec. 3, 2015

(65) Prior Publication Data
US 2017/0182257 A1      Jun. 29, 2017

(30) Foreign Application Priority Data

May 28, 2014   (EP) ................................. 14170332

(51) Int. Cl.
*A61M 5/24*     (2006.01)
*A61M 5/315*    (2006.01)
*A61M 5/31*     (2006.01)

(52) U.S. Cl.
CPC ........ *A61M 5/2448* (2013.01); *A61M 5/3155* (2013.01); *A61M 5/31528* (2013.01);
(Continued)

(58) Field of Classification Search
CPC .. A61M 5/24; A61M 5/2448; A61M 5/31551; A61M 2005/3125;
(Continued)

(56) References Cited

U.S. PATENT DOCUMENTS 5,240,146 A        8/1993   Smedley et al.
5,253,785 A   *   10/1993   Haber ..................... A61M 5/19
                                                      222/135

(Continued)

FOREIGN PATENT DOCUMENTS

EP      1603611        12/2005
JP      H8-503385       4/1996
(Continued)

OTHER PUBLICATIONS

International Search Report and Written Opinion in International Application No. PCT/EP2015/061619, dated Aug. 12, 2015, 13 pages.

(Continued)

*Primary Examiner* — Shefali D Patel
(74) *Attorney, Agent, or Firm* — Fish & Richardson P.C.

(57) ABSTRACT

A dose indicating mechanism for a drug delivery device is configured for delivery of a medicament contained in a single medicament cartridge, the medicament comprising at least a first drug and a second drug, wherein the dose indicating mechanism comprises a body, a dose dial component configured to move relative to the body during dose setting and a first dose indicator configured to display a set dose of the medicament, the first drug, or the medicament and the first drug depending on displacement of the dose dial component during the dose setting. In order to provide a user with further information, a second dose indicator is provided that is configured to display a set dose of the second drug (Continued)

during the dose setting. The disclosure is also directed to a respective drug delivery device.

23 Claims, 6 Drawing Sheets

(52) U.S. Cl.
CPC .... *A61M 5/31551* (2013.01); *A61M 5/31596* (2013.01); *A61M 5/31585* (2013.01); *A61M 2005/2407* (2013.01); *A61M 2005/3125* (2013.01); *A61M 2005/3126* (2013.01)

(58) Field of Classification Search
CPC ...... A61M 2005/3126; A61M 5/31528; A61M 5/3155; A61M 5/31596
See application file for complete search history.

(56) References Cited

U.S. PATENT DOCUMENTS

| | | | |
|---|---|---|---|
| 5,505,704 A * | 4/1996 | Pawelka | ................. A61M 5/19 604/191 |
| 2010/0324493 A1 | 12/2010 | Plumptre | |
| 2012/0330228 A1 * | 12/2012 | Day | ................. A61M 5/14244 604/82 |

FOREIGN PATENT DOCUMENTS

| | | | | |
|---|---|---|---|---|
| JP | 2000-070368 | 3/2000 | | |
| JP | 2003-010327 | 1/2003 | | |
| JP | 2013-512060 | 4/2013 | | |
| JP | 2013-539694 | 10/2013 | | |
| WO | WO 94/03392 | 2/1994 | | |
| WO | WO 2004/078239 | 9/2004 | | |
| WO | WO 2007/067889 | 6/2007 | | |
| WO | WO 2007/107431 | 9/2007 | | |
| WO | WO 2010/097125 | 9/2010 | | |
| WO | WO 2011/067187 | 6/2011 | | |
| WO | WO 2011/067267 | 6/2011 | | |
| WO | WO 2012049138 A1 * | 4/2012 | ........ | A61M 5/31535 |
| WO | WO-2012072533 A1 * | 6/2012 | ........ | A61M 5/31596 |
| WO | WO 2012/152703 | 11/2012 | | |
| WO | WO 2012/158138 | 11/2012 | | |
| WO | WO 2013/126173 | 8/2013 | | |

OTHER PUBLICATIONS

International Preliminary Report on Patentability in International Application No. PCT/EP2015/061619, dated Nov. 29, 2016, 8 pages.

* cited by examiner

DOSE INDICATING MECHANISM FOR A DRUG DELIVERY DEVICE AND DRUG DELIVERY DEVICE

CROSS-REFERENCE TO RELATED APPLICATIONS

This application is a U.S. national stage application under 35 USC § 371 of International Application No. PCT/EP2015/061619, filed on May 27, 2015, which claims priority to European Patent Application No. 14170332.2 filed on May 28, 2014, the entire contents of which are incorporated herein by reference.

TECHNICAL FIELD

The present disclosure is directed to a dose indicating mechanism for a drug delivery device configured for the delivery of a medicament contained in single medicament cartridge, the medicament comprising at least one first drug and at least one second drug. The dose indicating mechanism comprises a body and a dose dial component configured to move relative to the body during dose setting and first dose indicator means configured to display a set dose of the medicament and/or of the first drug in dependence of the displacement of dose dial component during dose setting. The disclosure is also directed to a drug delivery device comprising a respective dose indicating mechanism.

BACKGROUND

Drug delivery devices of the aforementioned kind are regularly used for the injection of a medicament out of a single cartridge into a patient and are adapted to receive or to be connected to the single medicament cartridge which can be accommodated in a cartridge holder attachable to a housing body. A distal portion of the cartridge holder may be adapted for receiving the medicament cartridge filled, wherein at the distal portion of the cartridge a needle assembly with an injection needle is attachable and wherein the proximal portion of the cartridge is adapted to at least partially receive a drive mechanism of the drug delivery device, the drive mechanism having a piston rod to become operably engaged with the piston of the cartridge for expelling a dose of the medicament from the cartridge. In order to set a dose, the drug delivery device comprises a dose dial component that is configured to rotate during dose setting. Such dose dial component can be configured as dose drum, a dose dial or a number sleeve.

Regularly the drug delivery devices are used by persons who do not have former medical training. Accordingly, the application comes along with circumstances that set a number of requirements for drug delivery devices of this kind. The patient has to be carefully informed about the dose of medicament he is about to inject after he has set his device. For that purpose, dose indicating mechanism are known in the art that display set dose values, dosage number or the like in correspondence with the set dose. These mechanisms comprises indicator means such a dosage number printed on the outer surface of number sleeve and are visible through a display window in the housing body, wherein the effective displayed dose value corresponds to the set dose of the medicament.

In WO 2007/067889 A1, a dose indicating assembly for a pharmaceutical injection device is described. The dose indicating assembly includes an external housing barrel extending in axial direction and a dial that is partially disposed within the housing barrel and which is screwably movable in axial direction relative to the barrel during dose setting. The dial includes an outer radial periphery with a plurality of parallel arrays of dose indicia provided thereon, which respectively represent a different drug concentration in the cartridge. Depending on the chosen concentration of the drug in the medicament cartridge, the first, the second or the third array is used to display the set dose.

WO 2012/158138 A1 describes an injection device with several dose setting windows for indicating a set dose of a medicament. A dose set sleeve is rotatably connected with a body for setting the desired dose and has a plurality of dosage numbers disposed thereon. A first helical pattern includes even numbers and a second helical pattern includes odd numbers. Non-number indicators separate the even numbers of the first helical pattern from the odd numbers of the second helical pattern. Upon rotating the dose set sleeve to set the desired dose, the dosage numbers are consecutively visible through the dosage indicator windows, wherein the numbers are alternately visible though the plurality of dosage indicator windows.

The dose information device described in WO 2007/107431 A1 is used in a medical administration device. A dose setting means is arranged to rotate during dose setting until a prescribed dose is visible in a dose window. After the dose setting member is rotated to set a dose, the dose is registered by a dose information member which is rotated until an indication is visible. When the dose is subsequently delivered, the dose information rotates such that when the dose is delivered, this prescribed dose is shown in the register information window indicating the patient as to which a subsequent dose is to be set.

The dose display mechanism described in WO 2011/067267 A1, comprises a dose setting dial with a first and a second indicating scale on its peripheral surface. The first and second helical dose indicating scales provide dose-related information in different orientations so that the dose information can be read by left-handed or and right-handed patients without the need to turn the device. The two dose indicating scales provide identical information in different orientation and both indicators display the entire set dose of medicament.

WO 2010/097125 A1 describes a dose setting mechanism with two windows through which scales on a dose setting member which rotates during dose setting and a dose limiting member that is operated by the physician prior to dose setting are visible. The dose limiting member is rotated until the prescribed dose size is visible in the window. Then, the dose limiting member is locked. To set a dose, the user turns the dose knob which causes the dose setting member to rotate. If the user tries to set a larger dose than preset, this is prevented by a stop surface of the dose limiting member.

SUMMARY

For combined therapy treatment, the known mechanisms are not suitable to sufficiently satisfy all needs for the therapy treatment. Certain therapies require the delivery of a combined formulation of active medicaments, respectively medicament drugs. If a patient requires a combination of medicines then there is an advantage if those medicines can be provided as a single formulation (i.e. both drugs are mixed together in predefined proportions and supplied in one primary pack) for delivery by a single injection device in one injection through a single needle. For example, in some cases it might be beneficial to treat a diabetic with a long acting insulin and with a glucagon-like peptide-1

(GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus. An example for another medicament combination is GLP-1 mixed with glucagon.

Accordingly, a single cartridge can be produced such that they contain a premix of medicaments such as a mix of a first drug A and a second drug B. Drug B may also be dissolved in the drug A so that B constitutes a component of the medicament A. Drugs A and B may be provided in different concentrations, accordingly. In order to provide the patient with information regarding the proportions of the medicaments he is about to inject, it is known to print the fixed ratio of the drugs on a label that is attached to the medicament cartridge or to the pen. However, when the dose to be injected is set, only the dose of the first medicament drug A (regularly the major drug in the medicament) or the entire set dose of the premix medicament is displayed to the user. When the patient or any medical personnel requires precise information about the medicament dose, respective calculations have to be performed. These calculations are expensive as to the fact that the required dose of the drug A is often flexible. Miscalculations may affect the effectiveness of the therapy.

Some aspects of the disclosure can be implemented to improve the dose setting properties of a drug delivery device in terms of safety and information content, in particular to improve information representation regarding the medicament composition of the injection the user is about to administer.

This is achieved by a dose indicating mechanism with the features of claim 1 and by a drug delivery device with the features of claim 14.

In particular, by providing a second dose indicator means that is configured to display a set dose of the second drug during dose setting, the user constantly receives information about the current dose value of the first drug A he is setting through the first dose indicator means as the dose dial component is displaced in accordance with a set dose of drug A. Simultaneously, he receives information about the dose value of the drug B he is setting. Calculations on the basis of the ratio between drug A and B are not necessary any more as the actual dose values are constantly displayed throughout the dose setting process. The first dose indicator means may be adapted to display a set dose of the entire medicament, which is effective when e.g. a drug B is dissolved in drug A. The first dose indicator means may also be adapted to display only a set dose of a proportion of the medicament, or a component which is effective when the medicament comprises two mixed substances with significant proportions, e.g. a mix of a drug A and a drug B.

A "drug" in the sense of the disclosure is to be understood as a medicament, but can also be a medicament component.

Examples of pen-type devices than can incorporate aspects of the present disclosure are described in EP 1 603 611 B 1. The mechanism is also suitable for other applications such as inhalers, ointment applicators or the like.

The EP 1 603 611 B1 application describes the structure and functionality of a pen-type injector or drug delivery device, specifically the interaction between the body and the dose dial component and also comprises a respective first dose indicator means to indicate the set dose of the medicament that is contained in the cartridge. A full description of the pen-type injection device is disclosed in EP 1 603 611 B1 is incorporated herein by reference.

It has been proven effective, when the first dose indicator and/or the second dose indicator means are configured to display dose values, preferably in terms of numbers. Other suitable dose-related information include dose indicating scales with indices such as dosage numbers, pointers, numerical or graphical symbols, digits or other suitable characters to provide the patient with accurate information regarding a set dose.

The dose dial component may be axially moveable with respect to the body, wherein first dose indicator means is configured such that the displacement or movement of the dose dial component causes the displayed dose to change. In a further embodiment, the dose dial component is rotatably arranged into the body. The dose dial component may also be in threaded engagement with the body, wherein the dose dial component may have a helical groove along an external surface of the dose dial component, wherein the body has a corresponding thread that is engaged with the helical groove of the dose dial component such that when a dose is set and the dose dial component is rotated with respect to the body, the dose dial component moves axially with respect to the body in a helical movement. The body may be configured as a housing or a housing element of the drug delivery device adapted to at least partially receive the dose dial component and may also be configured as a sleeve-like element.

According to a further embodiment, the second dose indicator means is coupled to the dose dial component in such way that the displayed dose value of the second dose indicator means changes in dependence of or in correspondence to the displacement or movement of the dose dial component. By coupling the second dose indicator means to the dose dial component, it can be ensured that the respective values of the set doses of the first and the second drug are displayed simultaneously. The first dose indicator means may be coupled to the dose dial component accordingly. Alternatively or additionally, the second dose indicator means may be coupled to the first indicator means in such way that the displayed dose value of second dose indicator means changes depending on the displayed value of the first dose indicator means.

According to a further embodiment, the displayed set dose of the second drug is in a fixed ratio with respect to the simultaneously displayed dose of the first drug. Preferably, the simultaneously presented value of the second dose indicator means is different to the value of the first dose indicator means. Both dose indicator means may be configured such that both dose indicators means display a set dose of zero units prior to dose setting when no dose is set.

Preferably, the ratio between simultaneously indicated set doses is unlike one. During dose setting, at a set dose greater than zero units, the ratio between the values of the first and second dose indicator means corresponds to the ratio between the first drug A and the second drug B and remains fixed during dose setting. In other words, during dose setting, the second dose indicator value increases at a ratio that is different to the ratio of the first dose indicator value.

In order to provide the patient with clearly visible information, the first dose indicator means and/or the second dose indicator means may comprises at least one dose scale. Further, the first dose indicator means and/or the second dose indicator may comprise an indicator such as a pointer, a colored marking or the like to indicate the set dose value by referring or pointing to the respective value on the scale.

According to a further embodiment, the first scale is different to the second scale. For example, the values on the first scale may increase at a different ratio than the values on the second scale. The scales are not only easier to distinguish but also enable the use of a common indicator, pointer or the like configured to move relative to the scales during dose setting. The first dose indicator means and the second dose indicator means may also share a common scale but are each provided with an own indicator such as a pointer or the like to indicate the value of the set dose on the scale.

In order to avoid confusion, both scales may be configured such that they are clearly distinguishable by the patient. Different scale types may be used. Further, the scales may have different size, color, orientation or position. For example, one scale may be rotationally provided on the dose dial component, while the other scale is provided on the outer surface of the body and is therefore stationary.

According to a further embodiment, the dose dial component is provided with dose-related information such as at least one dose scale or an indicator like a pointer or a colored marking or the like to indicate a value on a scale. Preferably, the dose-related information is provided on an outer peripheral surface of the dose dial component. For example, a number sleeve may be provided on its outer surface with dosage numbers.

According to a further embodiment, the first and/or the second dose indicator means comprise at least one movable element that is provided with dose-related information and that is coupled to the dose dial component such that displacement of the dose dial component causes displacement of the dose-related information and the respective displayed dose value to change. Thereby, the set doses of the first, respectively of the second drug can be efficiently displayed. For example, the movable element may be provided with a at least one dose scale which can be moved along a display window.

The movable element is preferably configured to move axially relative to the body, preferably inside the body. For this purpose, the movable element may be axially guided within the body, e.g. by an axially extending guidance such as a groove or the like, preferably on the inner surface of the body.

The body may be provided with dose-related information such as a scale, dosage numbers, graphical symbols or holes in the outer surface of the body configured to interact with at least one dose-related information on the movable element and/or on the dose dial component to indicate the set dose. The movable element and/or the dose dial component may comprise at least one corresponding indicator, such as a pointer, a colored marking or a colored bar. The movable element and/or the dose dial component may be provided with at least one scale, numbers or the like, wherein the dose-related information on the body may include at least one corresponding indicator such as at least one hole, a dose display window, a pointer or any other suitable indicator.

According to a preferred embodiment, on the outer surface of the body, a first scale for indicating a set dose of the first medicament drug is provided. Further, a second scale, which is preferably different to the first scale, may also be provided on the outer surface of the body. At least one corresponding indicating element, such as a preferably colored bar, a pointer or the like may move relative to the scales such as to indicate the set dose of the respective drug. This moving indicating means may be provided, e.g. on the dose dial component. Further, this indicating means may also be provided on the moving element. In each case, the indicating means moves relative to the scale, thereby indicating the set dose of the respective drug in correspondence to the displacement of the dose dial component.

In order to enable the patient to easily capture the information regarding the set dose, the body may be provided with at least one aperture such as a dose indicator window, which is arranged such that the first dose indicator value and/or the second dose indicator value are indicated by or visible through the aperture. Each of the apertures may be covered with a transparent cover such as a magnifying glass. The body may be provided with a first dose indicator window for displaying the dose value of the set dose of the first drug and a second dose window in the body for indicating the set dose of the second drug. This enables the patient to clearly differentiate between the first and the second drug. Preferably the dose windows have different sizes and/or shapes.

According to a further embodiment, the body comprises an elongated aperture for visually capturing dose-related information such as at least one indicator or at least one scale on the moving element. The aperture may also be configured to guide the movable element in axial direction.

According to a further embodiment, the body is provided with a number of apertures or holes serving as scale values, wherein a marking or the like on the movable element and/or on the dose dial component aligns respectively with one of the apertures during dose setting, thereby indicating that a certain dose is set. The apertures may be respectively marked with numbers or the like, the numbers corresponding to the value of the set dose.

According to a further embodiment, the first and or the second dose indicator means are adjustable e.g. in such way that the scales can be adjusted to different ratios of different premix medicaments. For example, a scale of the first dose indicator means and a scale of the second dose indicator means may be configured replaceable by using a replaceable sticker, a label or the like so that when a different premix is used, adapted scales are attached to the body.

Some aspects of the present disclosure can be solved by a drug delivery device comprising a respective dose indicator mechanism. Preferably, such drug delivery device comprises a medicament cartridge with the premixed medicament, the premixed medicament comprising a first drug and a second drug, wherein the ratio between the first and the second drug corresponds to the ratio between the displayed value of the first dose indicator means and the of the simultaneously displayed value of the second dose indicator means.

In particular, the advantages of the present disclosure make a positive difference when the pen-type injector is a disposable pen injection device. Such devices can be thrown away or recycled after the content of the medicament has been exhausted. The pen-type injector may be designed similar to that known from EP 1 603 611 B1.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N—(ω-carboxyheptadecanoyl)-des(B30) human insulin and B29-N—(ω-carboxyhepta-decanoyl) human insulin.

Exendin 4 for example means Exendin 4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin 4 derivatives are for example selected from the following list of compounds:

H-(Lys)4-des Pro36, des Pro37 Exendin 4(1-39)—NH2,
H-(Lys)5-des Pro36, des Pro37 Exendin 4(1-39)—NH2,
des Pro36 Exendin 4(1-39),
des Pro36 [Asp28] Exendin 4(1-39),
des Pro36 [IsoAsp28] Exendin 4(1-39),
des Pro36 [Met(O)14, Asp28] Exendin 4(1-39),
des Pro36 [Met(O)14, IsoAsp28] Exendin 4(1-39),
des Pro36 [Trp(O2)25, Asp28] Exendin 4(1-39),
des Pro36 [Trp(O2)25, IsoAsp28] Exendin 4(1-39),
des Pro36 [Met(O)14 Trp(O2)25, Asp28] Exendin 4(1-39),
des Pro36 [Met(O)14 Trp(O2)25, IsoAsp28] Exendin 4(1-39); or
des Pro36 [Asp28] Exendin 4(1-39),
des Pro36 [IsoAsp28] Exendin 4(1-39),
des Pro36 [Met(O)14, Asp28] Exendin 4(1-39),
des Pro36 [Met(O)14, IsoAsp28] Exendin 4(1-39),
des Pro36 [Trp(O2)25, Asp28] Exendin 4(1-39),
des Pro36 [Trp(O2)25, IsoAsp28] Exendin 4(1-39),
des Pro36 [Met(O)14 Trp(O2)25, Asp28] Exendin 4(1-39),
des Pro36 [Met(O)14 Trp(O2)25, IsoAsp28] Exendin 4(1-39), wherein the group —Lys6-NH2 may be bound to the C-terminus of the Exendin-4 derivative;

or an Exendin 4 derivative of the sequence
des Pro36 Exendin 4(1-39)-Lys6-NH2 (AVE0010),
H-(Lys)6-des Pro36 [Asp28] Exendin 4(1-39)-Lys6-NH2,
des Asp28 Pro36, Pro37, Pro38Exendin 4(1-39)—NH2,
H-(Lys)6-des Pro36, Pro38 [Asp28] Exendin 4(1-39)—NH2,
H-Asn-(Glu)5des Pro36, Pro37, Pro38 [Asp28] Exendin 4(1-39)—NH2,
des Pro36, Pro37, Pro38 [Asp28] Exendin 4(1-39)-(Lys)6-NH2,
H-(Lys)6-des Pro36, Pro37, Pro38 [Asp28] Exendin 4(1-39)-(Lys)6-NH2,
H-Asn-(Glu)5-des Pro36, Pro37, Pro38 [Asp28] Exendin 4(1-39)-(Lys)6-NH2,
H-(Lys)6-des Pro36 [Trp(O2)25, Asp28] Exendin 4(1-39)-Lys6-NH2,
H-des Asp28 Pro36, Pro37, Pro38 [Trp(O2)25] Exendin 4(1-39)—NH2,
H-(Lys)6-des Pro36, Pro37, Pro38 [Trp(O2)25, Asp28] Exendin 4(1-39)—NH2,
H-Asn-(Glu)5-des Pro36, Pro37, Pro38 [Trp(O2)25, Asp28] Exendin 4(1-39)—NH2,
des Pro36, Pro37, Pro38 [Trp(O2)25, Asp28] Exendin 4(1-39)-(Lys)6-NH2,
H-(Lys)6-des Pro36, Pro37, Pro38 [Trp(O2)25, Asp28] Exendin 4(1-39)-(Lys)6-NH2,
H-Asn-(Glu)5-des Pro36, Pro37, Pro38 [Trp(O2)25, Asp28] Exendin 4(1-39)-(Lys)6-NH2,
H-(Lys)6-des Pro36 [Met(O)14, Asp28] Exendin 4(1-39)-Lys6-NH2,
des Met(O)14 Asp28 Pro36, Pro37, Pro38 Exendin 4(1-39)—NH2,
H-(Lys)6-desPro36, Pro37, Pro38 [Met(O)14, Asp28] Exendin 4(1-39)—NH2,
H-Asn-(Glu)5-des Pro36, Pro37, Pro38 [Met(O)14, Asp28] Exendin 4(1-39)—NH2,
des Pro36, Pro37, Pro38 [Met(O)14, Asp28] Exendin 4(1-39)-(Lys)6-NH2,
H-(Lys)6-des Pro36, Pro37, Pro38 [Met(O)14, Asp28] Exendin 4(1-39)-(Lys)6-NH2,
H-Asn-(Glu)5 des Pro36, Pro37, Pro38 [Met(O)14, Asp28] Exendin 4(1-39)-(Lys)6-NH2,
H-Lys6-des Pro36 [Met(O)14, Trp(O2)25, Asp28] Exendin 4(1-39)-Lys6-NH2,
H-des Asp28 Pro36, Pro37, Pro38 [Met(O)14, Trp(O2)25] Exendin 4(1-39)—NH2,
H-(Lys)6-des Pro36, Pro37, Pro38 [Met(O)14, Asp28] Exendin 4(1-39)—NH2,
H-Asn-(Glu)5-des Pro36, Pro37, Pro38 [Met(O)14, Trp(O2) 25, Asp28] Exendin 4-(1-39)—NH2,
des Pro36, Pro37, Pro38 [Met(O)14, Trp(O2)25, Asp28] Exendin 4(1-39)-(Lys)6-NH2,
H-(Lys)6-des Pro36, Pro37, Pro38 [Met(O)14, Trp(O2)25, Asp28] Exendin 4(S1-39)-(Lys)6-NH2,
H-Asn-(Glu)5-des Pro36, Pro37, Pro38 [Met(O)14, Trp(O2) 25, Asp28] Exendin 4(1-39)-(Lys)6-NH2;
or a pharmaceutically acceptable salt or solvate of any one of the afore-mentioned Exendin 4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF DRAWINGS

In the following, aspects of the disclosure will be described by way of examples and with reference to the schematic drawings in which.

DETAILED DESCRIPTION

Figure 1:
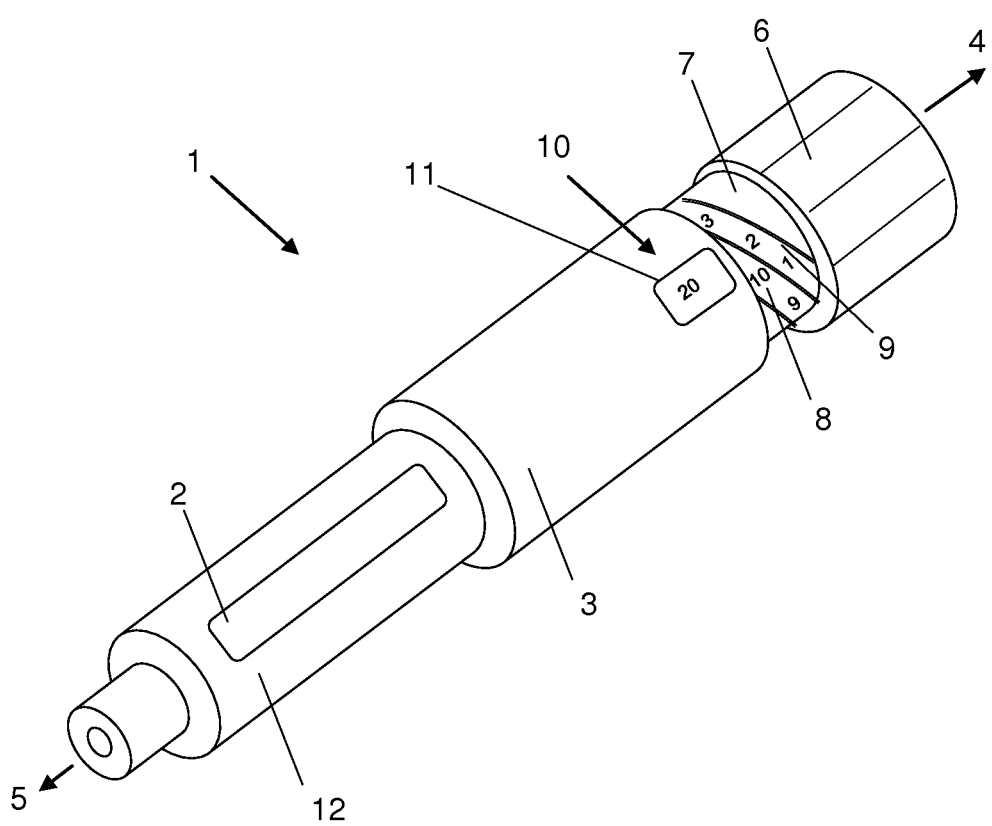

FIG. 1 shows a drug delivery device 1 for the delivery of a premixed medicament contained in a cartridge 2. The premix medicament comprises a first drug A, e.g. insulin, and a second drug B, e.g. GLP-1, that is mixed into the drug solution A. The drug delivery device 1 comprises a sleeve-like body 3 serving as a housing. The drug delivery device 1 extends from a proximal end 4 to a distal end 5. At the proximal end 4, a dial grip 6 is rotationally connected to a dose dial component 7 during dose setting, wherein the dose dial component 7 is configured as a number sleeve and has a plurality of dosage numbers 8 printed on its outer peripheral surface. The dose dial component 7 is in threaded engagement with the body 3 and has on its outer surface a helically extending groove 9 which engages a respectively formed thread (not shown) on the inner surface of the body 3 such that when the dose dial component 7 is rotated in a first direction during dose setting by rotating the dial 6, the dose dial component 7 winds out of the body 3 in proximal direction 4 and when the dose dial component 7 is rotated in the opposite direction during dose dispense, the dose dial component 7 winds into the body 3 in distal direction 5.

The dosage numbers 8 are distributed on the outer peripheral surface of the dose dial component 7 parallel to the helical groove 9. The body 3 is provided with first dose indicator means 10 that include the dosage numbers 8 and an aperture 11 in the body 3 serving as a dose window.

During dose setting, the dose dial component 7 rotates relative to the body 3 and moves in proximal direction. As a result, the dosage numbers 8 pass the window 11 and overlap with the window 11 successively, wherein the dosage number 8 that is presented through the window 11 corresponds to the currently set dose of the premixed medicament contained in the cartridge 2. The cartridge 2 is accommodated in a cartridge holder 12 at the distal end of the body 3. During dose setting, the user is not able to gain information about the amount of drug B he is setting or about to inject.

At the distal end of the cartridge holder 12, a dispense interface (not shown) such as an injection needle can be attached. In the body 3, a dose dispense mechanism (not shown) is disposed, the dose dispense mechanism comprising a piston rod, a lead screw or the like. During dose dispense, the piston rod moves in distal direction thereby displacing a bung in the cartridge 2 such that the medicament in the cartridge 2 is dispensed through the injection needle.

Figure 2:
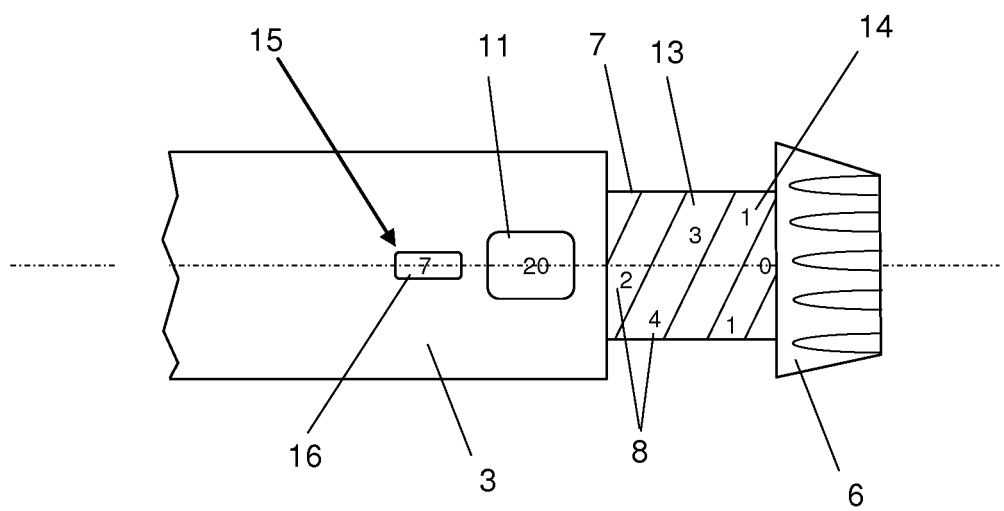
FIG. 2 shows a side view of a dose indicating mechanism in accordance with a first embodiment.

FIG. 2 shows the dose indicating mechanism in accordance with a first embodiment. On the outer surface of the dose dial component 7 are provided a first dose scale 13 and a second dose scale 14, each of the dose scales 13, 14 comprising dosage numbers 8 arranged on the outer surface of the dose dial component 7 in a helical pattern. The first dose scale 13 and the second dose scale 14 are arranged in a parallel relationship. The first dose scale 13 serves to display the set units of the drug A (e.g. insulin) in the cartridge. Generally, the first dose scale may also be configured to display the set dose of the premixed medicament.

The first dose scale 13 is arranged such that only the first dose scale 13 aligns with the first dose window 11 when the dose dial component 7 moves relative to the body 3 in helical movement, similar to the mechanism shown in FIG. 1. Second dose indicator means 15 comprise said second scale 14 and a second dose window 16 in the body 3. The second dose window 16 is arranged such that only the second dose scale 14 can align with the second dose window 16 when the dose dial component 7 moves relative to the body 3 in a helical movement.

When a user rotates the dial grip 6 up to 20 units as displayed in the first dose window 11 in FIG. 2, then 20 units of the drug A are dispensed in a subsequent injection step. At the same time, the value of the set dose of the second drug B is presented through the second dose window 16. The windows 11 and 16 have different sizes so that the user can clearly distinguish between the set doses of drug A and drug B. During dose setting, the dose values of drug A and drug B are visible through the first and the second dose window 11, 16 and constantly change during dose setting. The dosage number of the first dose scale 13 and the dosage number of the second dose scale 14 that are simultaneously visible through the respective dose window are in a fixed ratio to each other. The ratio between the two indicated dose values corresponds to the ratio between the first drug A and the second drug B contained in the cartridge 2. The first dose scale 13 and the second dose scale 14 are different such that the numerical values of the first dose scale 13 increase at a higher ratio than the numerical values of the second dose scale 14 when the dose dial component 7 is rotated.

Figure 3:
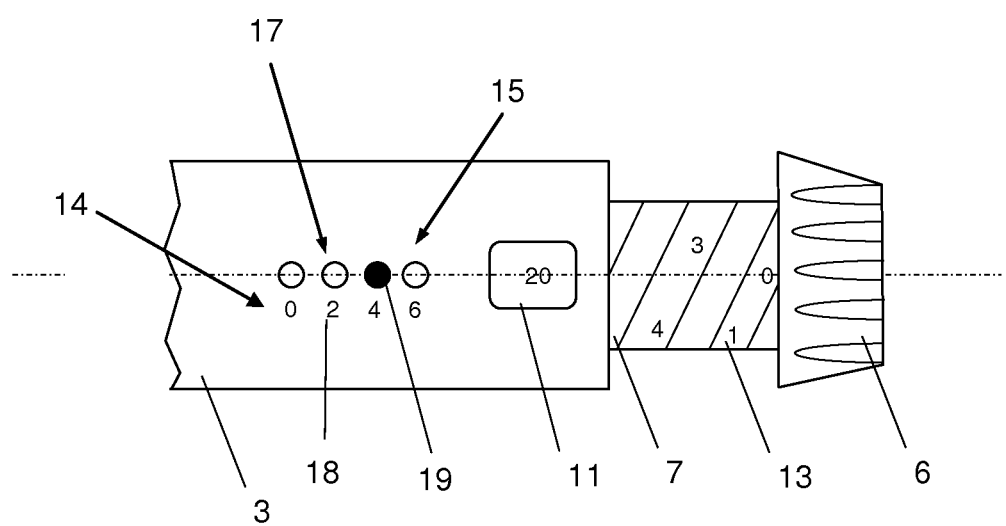
FIG. 3 shows a side view of a dose indicating mechanism in accordance with a second embodiment.

In FIG. 3, the second dose indicator means 15 includes four apertures or holes 17 in the body 3. The holes 17 are arranged in a row in axial direction of the body 3. Each of the holes 17 is provided with a dosage number 18. The dosage numbers 18 constitute the second dose scale 14. The dose dial component 7 comprises the first dose scale 13 with dosage numbers arranged in a helical pattern comparable to the embodiment in FIG. 2. During dose setting, the set dose of the first drug A is displayed through the first dose window 11 with the respective dosage number aligning with the dose window 11. The dose dial component 7 is also provided with a colored marking 19 serving as an indicator and arranged on the outer surface of the dose dial component 7. During dose setting, the colored marking 19 moves axially relative to the body 3 in accordance with the displacement of the dose dial component 7 in proximal direction. At the same time, the colored marking 19 moves past the holes 17 such that the colored marking 19 can be captured through one of the holes 17. When the colored marking 19 aligns with one of the holes 17, the set dose of the second drug B is indicated by the dosage number 18 of the hole 17 that is indicated with the colored marking 19.

Figure 4:
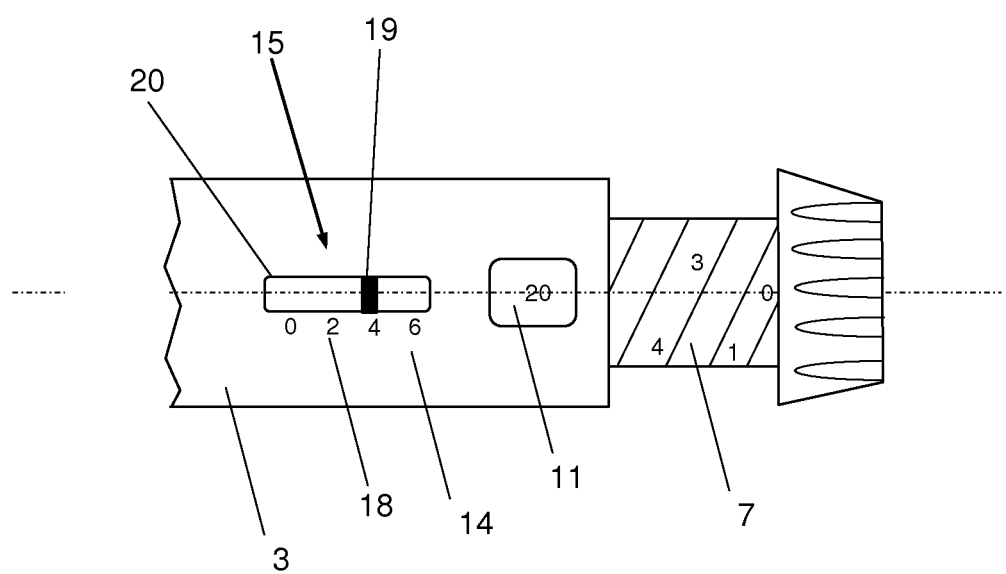
FIG. 4 shows a side view of a dose indicating mechanism in accordance with a third embodiment.

In FIG. 4, the body 3 is provided with an elongated aperture 20 as part of the second dose indicator means 15, the elongated aperture 20 extending in axial direction of the body 3. At the side edges of the elongated aperture 20, a second dose scale 14 is provided. The dose dial component 7 is provided with a bar-like colored marking 19 that moves axially in accordance with the dose dial component 7, thereby passing the single dosage numbers 18 in accordance with the set dose of the second drug B. The colored marking 19 can be a ring-like marking on the dose dial component 7. It is also possible to provide the dose dial component 7 with the second dose scale and the body 3 with the first dose scale.

Figure 5A:
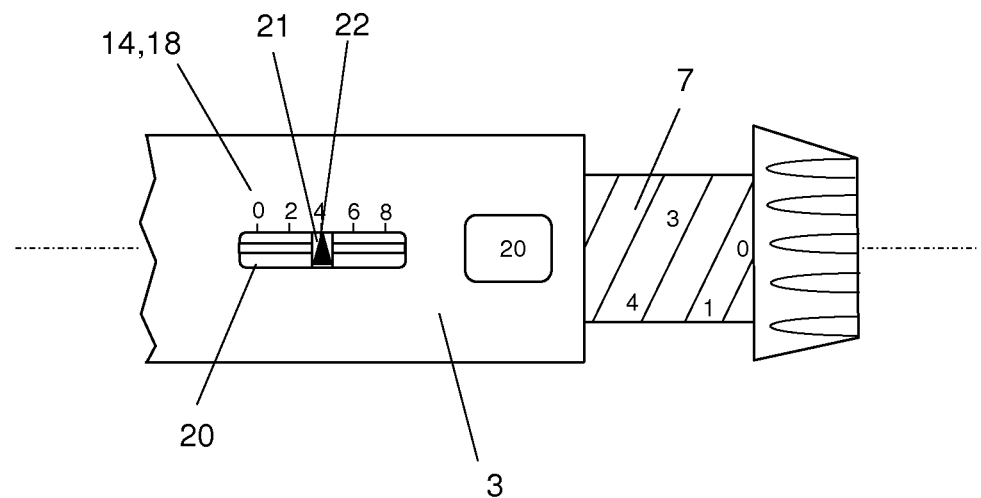
FIG. 5a, b show in side views a dose indicating mechanism in accordance with a fourth embodiment.
Figure 5B:
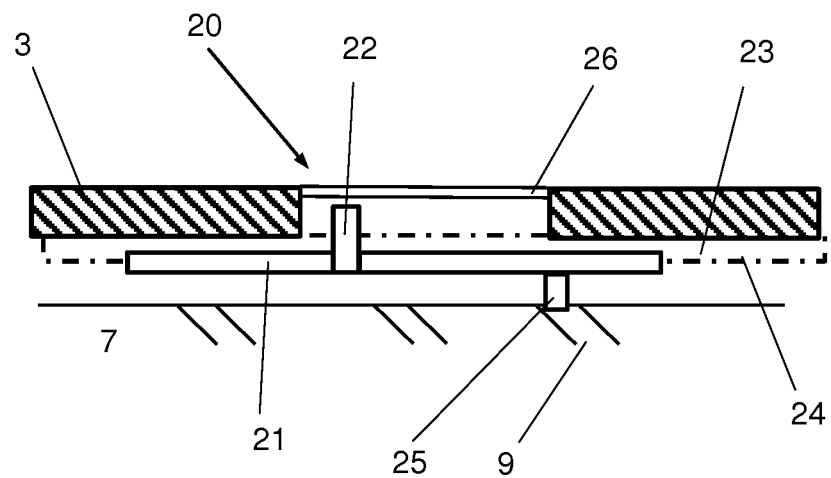

The embodiment in FIGS. 5a and 5b differs from the embodiment in FIG. 4 in that that has a movable element 21 with an indicator 22 in the form of a triangular pointer. The movable element 21 is axially guided in a groove 23 (FIG. 5b) on the inner surface 24 of the body 3 such that the movable element 21 can move axially with respect to the body 3 but cannot rotate. The movable element 21 is moved in axial direction by engagement with the helical groove 9 on the outer surface of the dose dial component 7. For this purpose, the movable element 21 has a thread element 25 which engages the helical groove 9. When the dose dial component 7 rotates, the movable element 21 is guided in axial direction depending on the rotation direction of the dose dial component 7. The second dose scale 14 is chosen such that the dose indicated by the interaction of the pointer 22 and the respective dosage number 18 on the second dose scale 14 indicates the set dose value of the second drug B. The aperture 20 is covered by a transparent cover 26.

Figure 6:
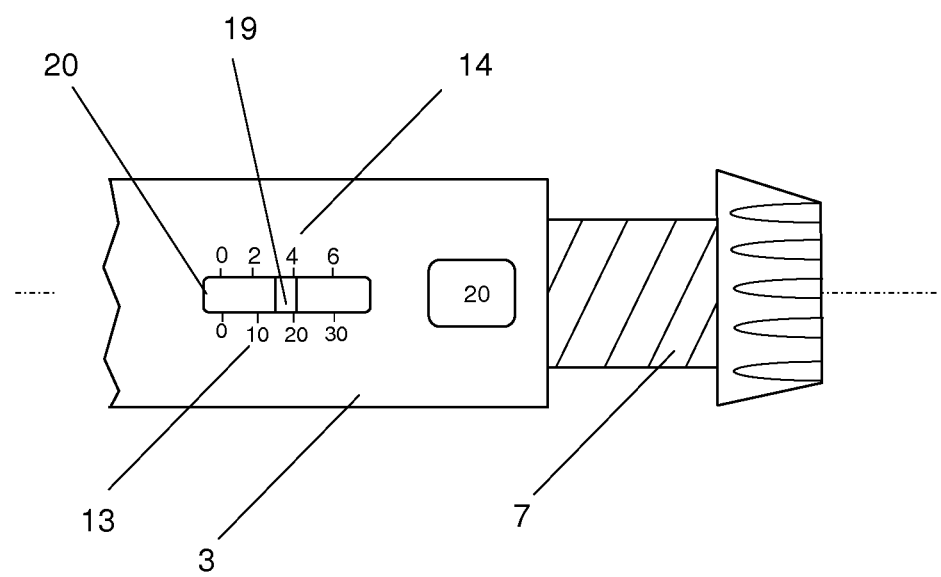
FIG. 6 shows a side view of a dose indicating mechanism in accordance with a fifth embodiment.

In the embodiment in FIG. 6, the dose dial component 7 is not provided with a first dose scale but the body 3 is provided with a first dose scale 13 and a second dose scale 14 provided on opposite sides of an elongated aperture 20. The dose dial component 7 is provided with a colored marking 19 which moves axially in accordance with the dose dial component 7 during dose setting such that the colored marking 19 moves relative to the dosage numbers 18 of the first and the second dose scale 13, 14. Alternatively, the colored marking 19 may be provided on a movable element as shown in FIGS. 5a and 5b.

As can be seen in FIG. 6, the first dose scale 13 is different to the second dose scale 14. Except for a set dose of zero units, the value of the set dose of the first drug A that is simultaneously indicated by the interaction of the colored marking 19 and the first dose scale 13 and the value of the set dose of the second drug B that is indicated by the interaction of the colored marking 19 and the second dose scale 14 are always in a fixed ratio to each other. For example, when a dose of 10 units of the first drug A is set, this is indicated by the colored marking 19 aligning with the 10-unit dosage number on the first dose scale 13. At the same time, the colored marking 19 aligns with the 2-unit dosage number on the second dose scale 14 indicating that a dose of 2 units is set of the second drug B. The ratio between the first and the second dose scale at this point is 5:1. When 20 units of the first drug are set, then there are set 4 units of the second drug. The fixed ratio corresponds to the ratio between the first and the second medicament drug in the medicament.

REFERENCE NUMERALS 1 drug delivery device
2 cartridge
3 body (housing)
4 proximal end
5 distal end
6 dial grip
7 dose dial component (number sleeve)
8 dosage number
9 helical groove
10 first dose indicator means
11 first dose window
12 cartridge holder
13 first dose scale
14 second dose scale
15 second dose indicator means
16 second dose window
17 holes
18 dosage number
19 colored marking (indicator)
20 elongated aperture
21 movable element
22 pointer (indicator)
23 groove
24 inner surface
25 thread element
26 transparent cover

The invention claimed is:

1. A dose indicating mechanism for a drug delivery device configured for delivery of a premixed medicament contained in a single medicament cartridge, the premixed medicament comprising at least a first drug and a second drug, wherein the dose indicating mechanism comprises:
a body;
a single dose dial component configured to move relative to the body during dose setting;
a single dial grip connected to the single dose dial component, the single dial grip being rotatable with the single dose dial component about a central axis of the drug delivery device, the single dial grip operable by a user to rotate the single dose dial component and to set a dose of the first drug contained in the single medicament cartridge and a dose of the second drug contained in the single medicament cartridge at the same time during the dose setting;
a first dose indicator configured to display a set dose of the premixed medicament, the set dose of the first drug, or both the set dose of the premixed medicament and the set dose of the first drug depending on displacement of the single dose dial component during the dose setting; and
a second dose indicator configured to display the set dose of the second drug during the dose setting,
wherein the displayed set dose of the second drug is in a fixed ratio with respect to the displayed set dose of the first drug.

2. The dose indicating mechanism according to claim 1, wherein the first dose indicator, the second dose indicator, or both the first dose indicator and the second dose indicator is configured to display dose values, dose units, or both the dose values and the dose units.

3. The dose indicating mechanism according to claim 2, wherein the second dose indicator is coupled to the single dose dial component, and wherein the displayed set dose of the second drug changes depending on the displacement of the single dose dial component.

4. The dose indicating mechanism according to claim 1, wherein the first dose indicator comprises a first dose scale.

5. The dose indicating mechanism according to claim 4, wherein the second dose indicator comprises a second dose scale, and wherein the first dose scale is different from the second dose scale.

6. The dose indicating mechanism according to claim 1, wherein the second dose indicator comprises a second dose scale.

7. The dose indicating mechanism according to claim 1, wherein the single dose dial component is provided with dose-related information on an outer peripheral surface.

8. The dose indicating mechanism according to claim 1, wherein the first dose indicator, the second dose indicator, or both the first dose indicator and the second dose indicator comprises at least one moveable element, and wherein the at least one moveable element comprises dose-related information and is coupled to the single dose dial component such that the displacement of the single dose dial component causes displacement of the dose-related information.

9. The dose indicating mechanism according to claim 8, wherein the at least one moveable element is configured to move axially relative to the body.

10. The dose indicating mechanism according to claim 9, wherein the at least one moveable element is axially guided within the body.

11. The dose indicating mechanism according to claim 8, wherein the body is provided with dose-related information and is configured to interact with the dose-related information of the at least one moveable element during the dose setting.

12. The dose indicating mechanism according to claim 1, wherein the body is provided with at least one aperture, wherein the at least one aperture is arranged such that the set dose of the first drug, the set dose of the second drug, or both the set dose of the first drug and the set dose of the second drug is indicated through the at least one aperture.

13. The dose indicating mechanism according to claim 1, wherein a moveable element, the single dose dial component, or both the moveable element and the single dose dial component comprises colored indicators.

14. The dose indicating mechanism according to claim 1, wherein the first drug, the second drug, or both the first drug and the second drug comprises a pharmaceutically active compound.

15. The dose indicating mechanism of claim 1, wherein the first dose indicator comprises a first dose scale provided on the dose dial component, and the second dose indicator comprises a second dose scale provided on the dose dial component.

16. The dose indicating mechanism of claim 15, wherein the first dose scale is arranged along a path on an outer surface of the dose dial component, the path along which the first dose scale is arranged being parallel to a path on the outer surface of the dose dial component along which the second dose scale is arranged.

17. The dose indicating mechanism of claim 16, wherein the path along which the first dose scale is arranged and the path along which the second dose scale is arranged are helical.

18. The dose indicating mechanism of claim 1, wherein the dose dial component is threadedly engaged with the body.

19. The dose indicating mechanism of claim 1, wherein the dose dial component is sleeve-shaped.

20. A drug delivery device configured for delivery of a premixed medicament comprising at least a first drug and a second drug, the drug delivery device comprising:
- a single medicament cartridge containing the premixed medicament; and
- a dose indicator mechanism comprising:
- a body,
- a dose dial component configured to move relative to the body during dose setting,
- a single dial grip connected to the dose dial component, the single dial grip being rotatable with the dose dial component about a central axis of the drug delivery device, the single dial grip operable by a user to set a dose of the first drug of the premixed medicament of the single medicament cartridge and a dose of the second drug of the premixed medicament of the single medicament cartridge at the same time during the dose setting,
- a first dose indicator configured to display the set dose of the first drug during the dose setting, and
- a second dose indicator configured to display the set dose of the second drug during the dose setting,
- wherein a ratio between the first drug and the second drug corresponds to a ratio between the displayed set dose of the first drug and the displayed set dose of the second drug.

21. The drug delivery device according to claim 20, wherein the first dose indicator, the second dose indicator, or both the first dose indicator and the second dose indicator is configured to display dose values, dose units, or both the dose values and the dose units.

22. The drug delivery device according to claim 21, wherein the second dose indicator is coupled to the dose dial component, and wherein the displayed set dose of the second drug changes depending on displacement of the dose dial component.

23. The drug delivery device according to claim 20, wherein the dose dial component is provided with dose-related information on an outer peripheral surface.

* * * * *